United States Patent [19]

Martin

[11] Patent Number: 4,859,183

[45] Date of Patent: Aug. 22, 1989

[54] ROOT CANAL INSTRUMENT HANDLE

[76] Inventor: Howard Martin, 909 Pershing Dr., Silver Spring, Md. 20910

[21] Appl. No.: 222,020

[22] Filed: Jul. 21, 1988

[51] Int. Cl.⁴ .................................................. A61C 1/14
[52] U.S. Cl. .................................................... 433/102
[58] Field of Search .......................................... 433/102

[56] References Cited

U.S. PATENT DOCUMENTS 3,247,594  4/1966  Nosonowitz ......................... 433/102
4,280,808  7/1981  Johnsen et al. ..................... 433/141

Primary Examiner—Robert Peshock

[57] ABSTRACT

An improved root canal instrument is provided having a novel handle. This handle is provided for a root canal file. This novel handle is formed and/or constructed of spaced cylindrical portions having grooves located between the cylindrical portions. The handle 14 is provided with flat sides 20. Theses flat sides have grooves formed and/or constructed therein. The shape of the grooves is inconsequential. They may be V-shaped or of other desired forms so long as they run across both the flat and curved portions of the handle.

3 Claims, 1 Drawing Sheet

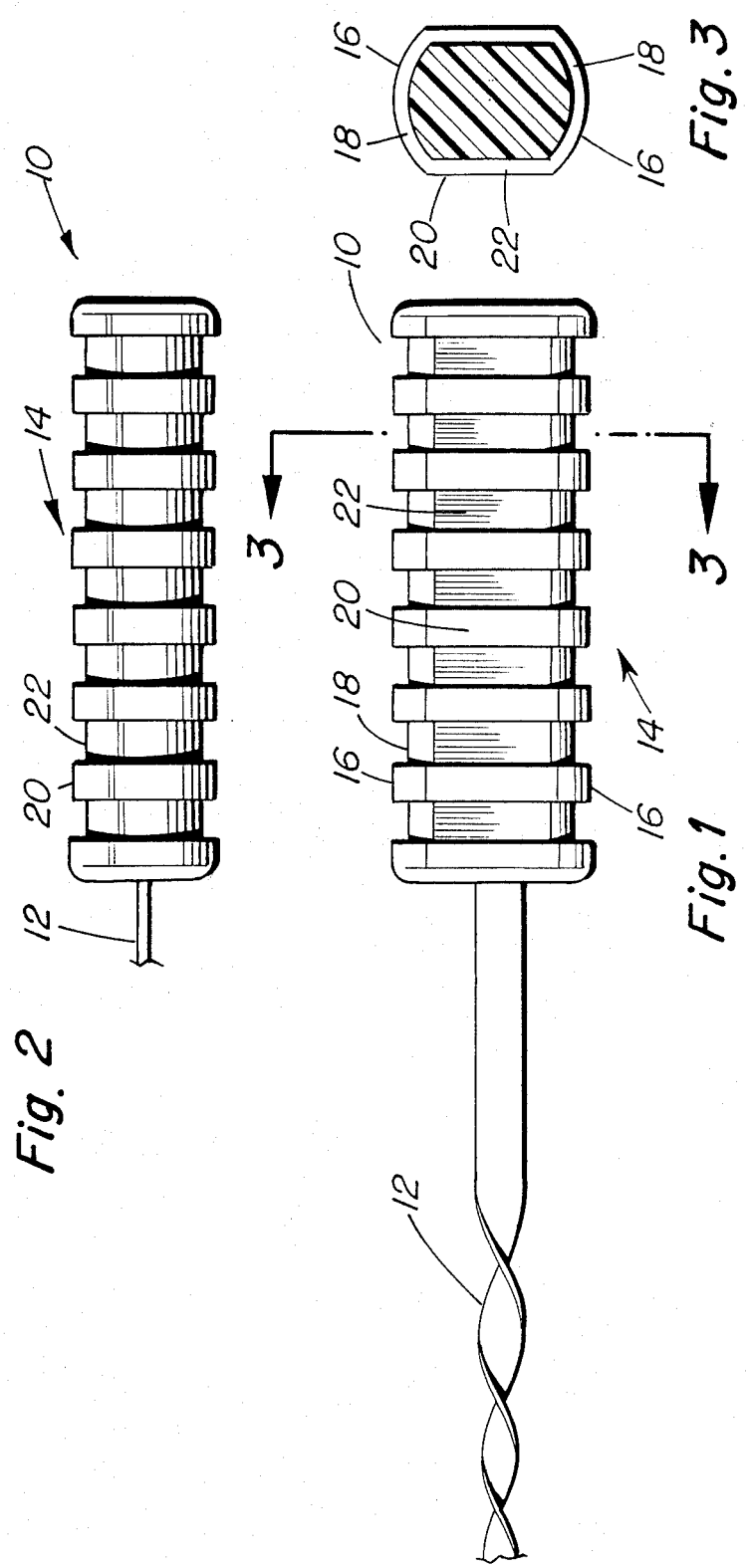

ROOT CANAL INSTRUMENT HANDLE

BACKGROUND AND SUMMARY OF THE INVENTION

This invention relates to dental apparatus, and more particularly it relates to a root canal handle file.

All root canal hand files are powered by the operator dentist thumb and forefinger. It takes a tactile sense to properly manipulate the file within the canal so that the cutting and shaping of the canal is correctly accomplished.

This is the first handle based upon an accumulation of 25 years of endodontic research that adapts the power source, the dentist's fingers, to the means, the file handle, that controls and places the power drive onto the cutting flutes of the file.

The operators fingers must gain total control and feel of the file in order to cut and debride the canal properly and completely. All canals are curved in one direction or another and, therefore, the file is curved accordingly. This requires even greater control by the operator and this is achieved through the new handle of this invention. Controlled power is passed through the dentist's fingers into the handle directing and guiding the cutting blade of the file within the confines of the root canal.

Root canal preparation is accomplished by a hand instrument called a root canal file. The root canal file achieves its cutting on a withdrawal stroke within the canal. The withdrawing action of the file can be effected in either a filing (rasping) or reaming (drilling) motion.

In a filing motion the instrument is placed into the canal at the desired length, pressure is exerted against the canal wall and while maintaining this pressure, the instrument is withdrawn without turning. The angle of the flutes effect a cutting action as the instrument is withdrawn.

The entire length and circumference of large diameter canals can be filed by inserting the instrument to the desired working length and filing circumferentially around the walls. The usual root canal instrument handle has been a serrated or ribbed cylinder or a peanut shaped cylinder to increase tactile sense and control through the depression in the instrument to accommodate the bulge in the fingers.

The fingers that hold the root canal instrument are the thumb and forefinger. The mechanical control and tactile sense have not taken into consideration the reciprocal action required in root canal file preparation action. Also, with the advent due to infection control, of the dentist wearing gloves a surer means of control is now required.

The second or alternative action of canal preparation is to use the same file in a reaming action, the motion being penetration, rotation and retraction. The file will set in the dentin and must, therefore, be treated carefully. Withdrawing the file cuts away engaged dentin. However, this requires a turning or twisting action on the part of the fingers holding the file handle.

A cylindrical handle will lack the one quarter turn control required while if gloves are used will cause a rippling or bagging of the glove. Files therefore should be generally used in a push pull motion with a controlled ability to turn or twist. This can only be accomplished by a properly designed handle to take into account the latest morphological results and modern armentarium.

It has been shown that twisting the file locks it into the dentin, leading to early fracture or ledge formation. Also, twisting the file in the apical area of the canal has been shown to cause a zip, perforation, or ledge. All are results of not controlling the file in a reciprocal mode.

Another deviation is that twisting the file will cause an elbow formation within the canal as the file tends to cut on one side of the canal only. This is another reason why control through the handle is critically important. A file can be rotated but only in a small size and at the apex. The rotation is never more than a one quarter turn. This is not controllable with the present hands. The filing action, which is properly a reciprocal motion, is necessary to create a proper retention and resistance form in the apical third for eventual filling of the canal. As most canals are ovoid, filing is the required action in the middle and cervical portions of the canal.

To summarize the basic action of root canal files, it is that they may be used to ream out a canal by the one quarter turn push-pull method, but that files are to be generally used as a straight push-pull instrument to enlarge by rasping canal as well as the ovoid portion of canals.

The power source for a root canal file is the dentist's thumb and forefinger grasping the file handle between the two. The one quarter turn is best analogous to winding a wristwatch. The push pull is simply a controlled up and down reciprocal movement.

The new improved handle has two parallel flat sides with a curved portion between. The operator holds between thumb and forefinger the flat sides, gloved or ungloved, and is easily able to control the reciprocal action of the file and avoids any glove problem.

If desirous of the one quarter turn method then the one quarter turn is easily accomplished from the flat sides by sliding the forefinger down shorter than the thumb and the edge will keep the operator within one quarter turn. The sides of the flat portion are also ribbed horizontally in order to add further surface area as well as enhance control and adaptation. Now the dentist has total control of his power source, his fingers, through the handle of this invention, to the cutting blade of the file and can now precisely control the mechanical preparation of the root canal with a controlled precision handle.

As stated, previously and presently, all handles are either cylindrical or peanut shaped. This new improved handle concept is based upon the morphology of the root canal, how a file cuts, and the spatial geometry of a properly prepared root canal designed to receive a filling material. It brings to bear on the handle the vertical and twisting pressures exerted on the blade within the canal in a logical and functional manner enabling the operator to always know where he is within the canal preparation.

It is ergonomically sound as it requires less stress on the fingers and wrist with increased control allowing for a more efficient, effective and easy preparation with reduced fatigue due to less twisting of the wrist. The dual flat ribbed handle allows for easier preparation of the severely curved canal by the ability to force the handle in the opposite direction of the curve enabling the dentist controlling the instrument to properly and smoothing and clearing the curvature.

Therefore the new improved root canal handle is based upon scientific parameters and biologic principles. It is a handle that can be made of metal, plastic, silicone or any other suitable material. The handle will be color coded accorded to the ADA, ISO specifications to match the file blade size. It may have the size number imprinted upon itself.

The ribs go completely around the handle or may only be on the flat side. Colors are—06-pink; 08-gray; 10-purple; 15-white; 20-yellow; 25-red; 30-blue; 35-green; 40-black; and repeated to 140.

It is an object of this invention to provide a new root canal handle that enables the energy developed to be properly transmitted to the root canal file so that the force creates a properly prepared canal shape in a spatial geometry mode.

Another object of this invention is to provide a novel root canal handle that has a push pull action developed and by the flat sides of the handle to transfer the energy so that the cutting and dentin removing aspect creates the proper apical shape with the root canal.

To provide a root canal handle that is economical to construct, easy to operate, and efficient in operation, is another object of this invention.

And another object of this invention is to provide a root canal handle for a root canal file that uses a tactile sense to properly manipulate the file within the canal so that the cutting and shaping of the root canal is correctly accomplished.

To provide a root canal handle that adapts the power source, the dentist's fingers, to the means, the file handle, that controls and places the power derived onto the cutting flutes of the file.

Further objects and advantages of the invention will become more apparent in light of the following description of the preferred embodiments.

BRIEF DESCRIPTION OF THE DRAWINGS

FIG. 1 is a side elevation of an improved root canal instrument handle for a root canal file;

FIG. 2 is a plan looking down on improved root canal instrument handle FIG. 1; and FIG. 3 is a cross-section of the improved root canal instrument handle taken along line 3—3 of FIG. 1.

It is to be noted that the scale of the drawings is approximately 10 times+actual size.

DESCRIPTION OF THE PREFERRED EMBODIMENTS

Referring now to FIGS. 1 to 3 of the drawings, there is shown an improved root canal instrument 10 having a handle 14 for a root canal file 12. The handle 14 is formed and/or constructed of spaced cylindrical portions 16 having grooves 18 located between the cylindrical portions 16.

The handle 14 is provided with flat sides 20, best shown in FIG. 3. These flat sides 20 have grooves 22 formed and/or constructed therein.

The shape of grooves 18 and 22 is inconsequential. They may be V-shaped or of other desired forms so long as they run across both the flat and the curved portions of the handle 14.

In operational use, the tactile sense of the dentist operator is properly used to manipulate the file 12 within the root canal so that the cutting and shaping of the canal is correctly accomplished. The handle 14 is adapted to control the power source, the dentist's fingers, to the means, the file handle, that controls and places the power drive into the cutting flutes of the file 12. The operator's fingers gain total control and feel of the file 12 in order to cut and debride the canal properly and completely. All canals are curved in one direction or another and therefore the file 12 is curved accordingly. This requires even greater control by the operator. This is achieved through the new and novel handle 14. Controlled power is passed through the dentist's fingers into the handle 14 directing and guiding the cutting blade of the file 12 within the confines of the root canal.

As can be readily understood from the foregoing description to the invention, the present structure can be configured in different modes to provide a device for playing a plurality of games.

Accordingly, modifications and variations to which the invention is susceptible may be practiced without departing from the scope and intent of the appended claims.

What is claimed is:

1. A root canal handle for use with a root canal instrument having a file positioned in said handle, comprising, a substantially elongated member formed in the shape of a handle for use with a root canal file, said handle having oppositely spaced substantially cylindrical portions running in the longitudinal direction thereof, said substantially cylindrical portions having spaced grooves located between said oppositely spaced cylindrical portions and arranged substantially transversely to the longitudinal direction of said handle, said handle having substantially spaced flat opposite sides positioned between said oppositely spaced cylindrical portions and spaced from each other, with said substantially spaced flat sides having grooves formed therein and arranged substantially transversely to the longitudinal direction of said handle.

2. A root canal handle for use with a root canal instrument as recited in claim 1, wherein said grooves are substantially V shaped.

3. A root canal handle for use with a root canal instrument as recited in claim 1, wherein said grooves run substantially across both said flat sides curved portions of said handle.

* * * * *